United States Patent
Schröder

(10) Patent No.: US 7,414,738 B2
(45) Date of Patent: Aug. 19, 2008

(54) MEASURING DEVICE FOR MEASURING THE DEGREE OF TRANSMISSION OF A COATING

(75) Inventor: Jürgen Schröder, Grosskrotzenburg (DE)

(73) Assignee: Applied Materials GmbH & Co. KG., Alzenau (DE)

( * ) Notice: Subject to any disclaimer, the term of this patent is extended or adjusted under 35 U.S.C. 154(b) by 364 days.

(21) Appl. No.: 10/883,561

(22) Filed: Jul. 1, 2004

(65) Prior Publication Data

US 2005/0264829 A1 Dec. 1, 2005

(30) Foreign Application Priority Data

Jun. 1, 2004 (EP) ................................ 04012900

(51) Int. Cl.
*G01B 11/28* (2006.01)
(52) U.S. Cl. ..................................... 356/630
(58) Field of Classification Search ............. 356/239.1, 356/443, 432, 72, 632
See application file for complete search history.

(56) References Cited

U.S. PATENT DOCUMENTS

| | | | |
|---|---|---|---|
| 4,765,273 A | 8/1988 | Anderle | |
| 4,981,566 A | 1/1991 | Wurczinger | |
| 5,396,080 A * | 3/1995 | Hannotiau et al. | 250/559.28 |
| 6,194,701 B1 | 2/2001 | Task et al. | |
| 6,359,686 B1 * | 3/2002 | Ariglio et al. | 356/239.1 |
| 6,392,754 B1 * | 5/2002 | Pingel et al. | 356/603 |
| 6,657,439 B1 * | 12/2003 | Harada | 324/600 |
| 6,797,407 B2 * | 9/2004 | Kato | 428/626 |
| 2002/0186381 A1 | 12/2002 | Subrahmanyan et al. | |
| 2004/0206024 A1 | 10/2004 | Graf et al. | |

FOREIGN PATENT DOCUMENTS

| | | |
|---|---|---|
| DE | 1 1 95 135 | 6/1965 |
| DE | 38 06 382 A1 | 9/1989 |
| DE | 3925536 A1 | 2/1991 |
| DE | 4127701 | 2/1993 |
| DE | 42 01 274 A1 | 7/1993 |
| DE | 101 41 897 C1 | 8/2001 |
| EP | 0 324 351 A2 | 7/1989 |
| EP | 0553004 | 7/1993 |
| GB | 2 029 017 A | 3/1980 |

\* cited by examiner

*Primary Examiner*—Tarifur R. Chowdhury
*Assistant Examiner*—Isiaka O Akanbi
(74) *Attorney, Agent, or Firm*—Fulbright & Jaworski L.L.P.

(57) ABSTRACT

The invention relates to a measuring device for measuring the degree of transmission of a coating on a glass plate. The glass plate rests on a support relative to which it is shifted. The support is provided with a gap enabling a light beam to pass through the glass plate and to impinge on a light receiver. Thus, the degree of transmission of the coating can be determined. Further, the reflection and the electric resistance of the coating can be measured by the measuring device.

8 Claims, 2 Drawing Sheets

Figure 3:
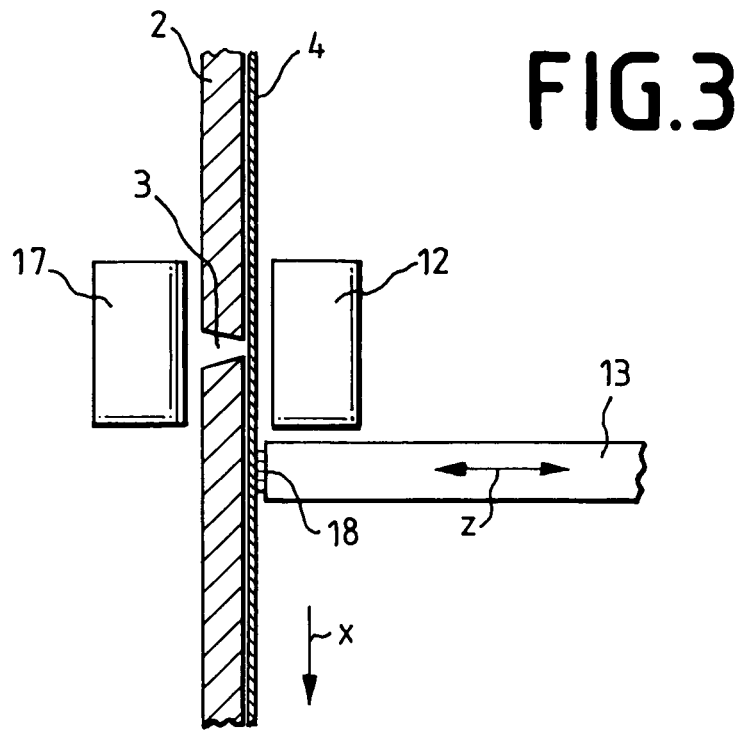

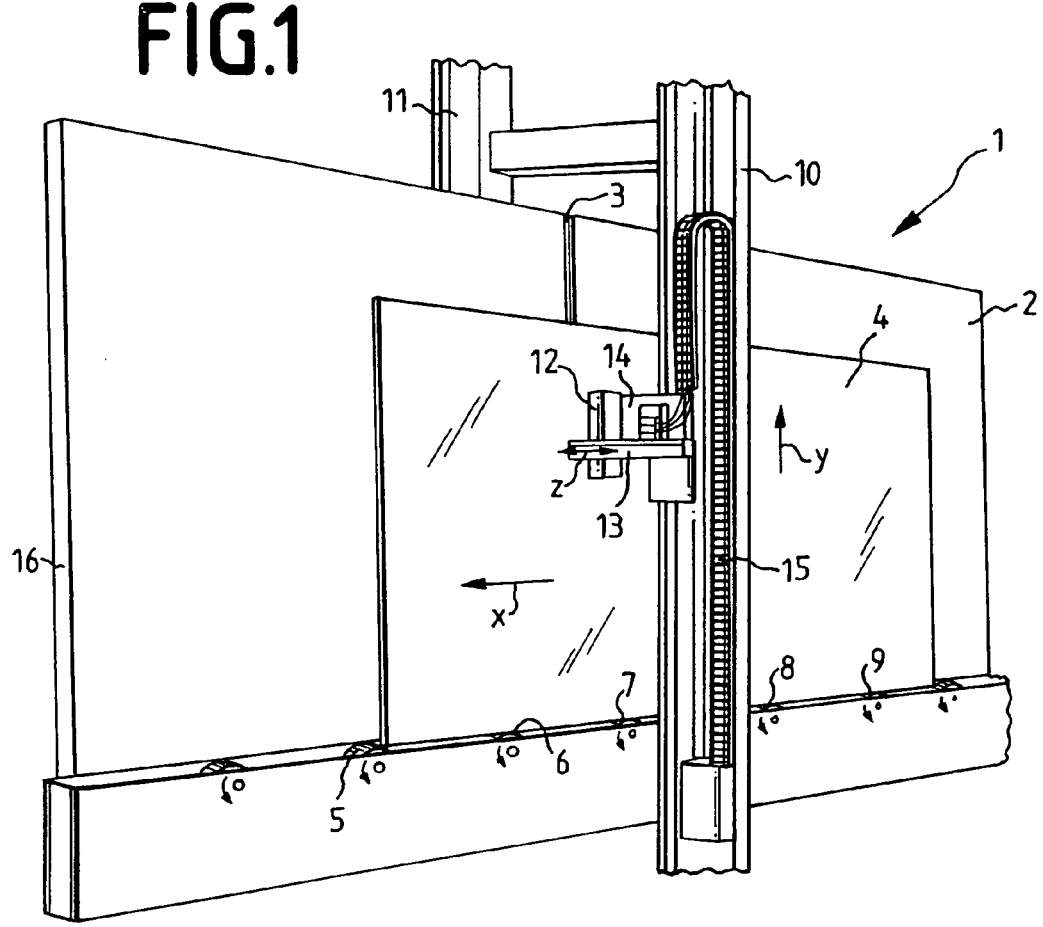
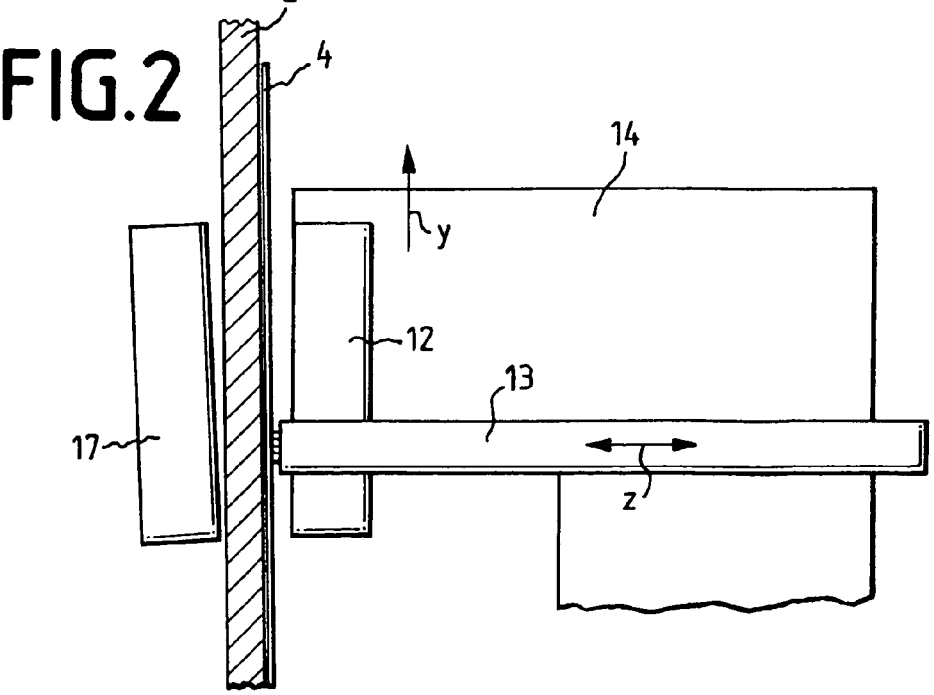

MEASURING DEVICE FOR MEASURING THE DEGREE OF TRANSMISSION OF A COATING

This application claims priority from European patent application no. 04 012 900.9 filed Jun. 1, 2004, incorporated herein by reference.

The invention relates to a measuring device according to the preamble of patent claim 1.

The coating of substrates, for example of glass plates by means of sputtering, should be as uniform as possible. Only if the coatings have the same thickness over the entire substrate, is it ensured that the optical properties, such as transmission, reflection and electrical resistance of the coatings are identical at all sites.

Measuring these optical properties conventionally takes place on coated substrate samples. Substrate samples are removed and tested in the laboratory, which entails considerable time expenditures. This applies in particular to the characterization of large-area coatings, since in this case a large number of samples must be taken and tested. With good spatial resolution approximately 80 hours of work are required for the acquisition of the spectral reflection, the spectral transmission and the surface resistance over the entire sample.

The invention therefore addresses the problem of acquiring automatically the essential optical properties of a coating.

This problem is solved according to the characteristics of patent claim 1.

The advantage attained with the invention comprises in particular that the transmission of a coated plate-form substrate can be automatically measured at all surface points. In one embodiment of the invention it is moreover possible to measure additionally the spectral reflection and the surface resistance of the coating automatically. As a rule, flat glass with a thickness of 0.5 mm to 6 mm is utilized as the substrate, where the size of the glass plate can be approximately 2.2 m×2.4 m. The measuring sites on the glass plate, which can be arbitrarily selected, are approached with an absolute accuracy of <5 mm and a relative accuracy <1 mm. The measuring rate is more than 1000 measurements per hour with the simultaneous measuring of the transmission $T(\lambda)$, the reflection $R(\lambda)$ and the surface resistance R. If only $T(\lambda)$ and $R(\lambda)$ are measured, more than 2000 measurements per hour are possible. The measurement of the surface resistance is carried out according to the four-point method, in which the measuring range is between 10 m$\Omega$ and 1000 $\Omega$. The thickness of the coating on the glass can be calculated from the measurements of $T(\lambda)$ and $R(\lambda)$.

Figure 4:
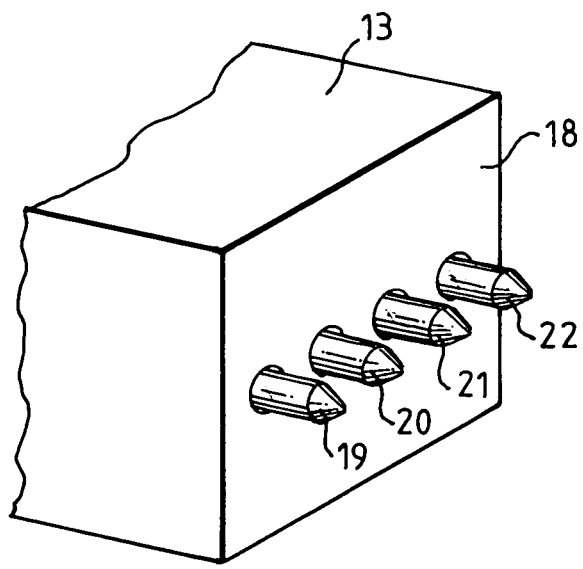
Figure 5:
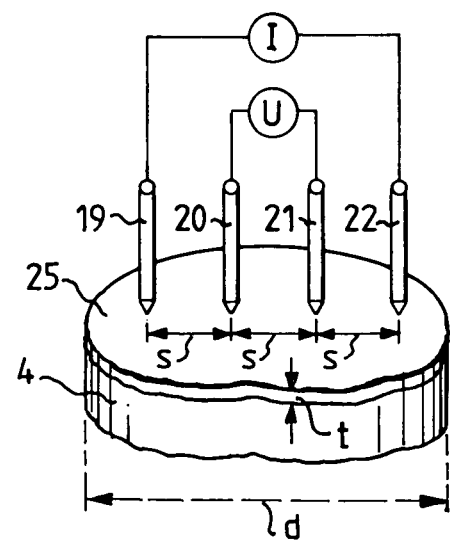

An embodiment example of the invention is shown in the drawing and will be described in further detail in the following. In the drawing depict:

FIG. 1 a support plate with glass plate and measuring instruments,

FIG. 2 an enlarged partial view from FIG. 1,

FIG. 3 a top view onto the device according to FIG. 2,

FIG. 4 the end of a resistance measuring head,

FIG. 5 a configuration for the four-point resistance measurement.

FIG. 1 depicts a device 1 for measuring parameters or properties of a coating of a substrate. This device 1 comprises a support plate 2, which is provided with a vertical slot 3 in the center. In front of this support plate 2 is disposed a coated glass plate 4 which rests on rollers 5 to 9 at an angle between 48 and 108 relative to the vertical. The glass plate 4 is here provided on its side facing away from the support plate 2 with a coating applied, for example, by means of a sputtering process. Through nozzles, which are not shown in FIG. 1, air flows into the space between glass plate 4 and support plate 2 such that the glass plate rests on an air cushion. Further details in this connection are described in the PCT application PCT/EP 2004/002333.

The rollers 5 to 9 are synchronously rotated clockwise or counterclockwise by a motor, not shown in FIG. 1. Through such a rotation the glass plate 4 is shifted either toward the right or the left relative to the stationary support plate 2.

Also disposed stationarily are two columns 10, 11 of which one column 10 is provided in front of the support plate 2 and one column 11 behind the support plate 2. These columns 10, 11 support measuring instruments which are vertically movable, i.e. in the Y-direction. One of the measuring instruments 12 is a reflection measuring instrument, while the other measuring instrument 13 is a resistance measuring head. Both measuring instruments 12, 13 are fastened on a carriage 14. The movement of the measuring instruments 12, 13 in the Y direction takes place via a not shown belt drive integrated into the column 10, which moves the carriage 14. The supply lines and measuring cables for the measuring instruments 12, 13 are guided in the drag line device 15. Similar to column 10, column 11 also supports a measuring instrument, which, however, is only a light-receiving measuring instrument and not evident in FIG. 1, but which, like the optical measuring instrument 12, is disposed directly in the proximity of gap 3.

The glass plate 4 is transported in three phases: first, said air cushion is generated between support plate 2 and glass plate 4. Subsequently the rollers 5 to 9 are rotated, which, due to the friction force between rollers 5 to 9 and the lower edge of the glass plate 4, move the glass plate 4 in the X-direction. After it has reached a specified measuring position, the air is switched off such that the air cushion is collapsed again.

During the measuring process the resistance measuring head 13 is in contact on the coating. In order to carry out the next measuring process, it must be moved away from the coating. Consequently, if it carries out several measurements sequentially, the resistance measuring head 13 completes a movement back and forth in the Z direction.

FIG. 2 shows a view onto an edge 16 of the support plate 2. It can be seen that in front of the glass plate 4 is disposed the reflection measuring instrument 12. Behind the glass plate 4 is disposed a transmission measuring instrument 17. The transmission measuring instrument acquires the intensity of the illumination source contained in the reflection measuring instrument, reduced by the reflection and absorption losses of the layer or of the glass plate 4. It consequently acquires the intensity of the light passing through the sample. The reflection measuring instrument 12 and the transmission measuring instrument 14 move synchronously in the Y direction. The light source in the reflection measuring instrument 12 consequently illuminates the coating of the glass plate 4 as well as also the transmission measuring instrument 17. This transmission measuring instrument 17 is slightly inclined relative to the support plate 2, so that the rays reflected by its sensor are not projected back into it by the sample. The support plate 2 and the glass plate 4 are minimally inclined toward the left, in order for the glass plate 4 not to fall down toward the right.

The resistance measuring head 13 is secured on the same carriage 14 as the reflection measuring instrument 12. Both instruments have a specific distance from one another in the X direction, but are moved synchronously in the Y direction. The reflection measuring instrument 12 can be, for example, the model "Zeiss Corona D vis".

FIG. 3 shows a view from above onto the essential structural elements of FIG. 2. It is evident that the reflection measuring instrument 12 and the transmission measuring instrument 17 are disposed opposite to one another at the level of gap 3. Hereby the rays of light can traverse unhindered by the support plate 2 from the reflection measuring instrument 12 to the transmission measuring instrument 17. The white light source located in the reflection measuring instrument 12 supplies the light for the reflection measurement as well as also for the transmission measurement. The transmission measuring instrument 17 can be the model "Zeiss Corona TV vis".

FIG. 4 shows the end 18 of the resistance measuring head 13. Visible are four pins 19, 20, 21, 22, which are spring-mounted. With these four pins 19 to 22 it is possible to carry out a so-called four-point measurement on the coating of the glass plate. Pins 19 to 22 are supported on springs and have a pressure point, whereby all four pins 19 to 22 exert in each instance the same force onto the coating. The resistance measuring head 13 itself is spring-mounted, and the adjustable spring force of the resistance measuring head is minimally greater than the sum of the four spring forces of pins 19 to 22.

Bending the glass plate 4 by the pressure exerted by pins 19 to 22 is prevented through the support plate 2, on which the glass plate 4 rests.

The distance between the optical measuring axis of the optical measuring instruments and the site of the resistance measurement is a specified value, such that, when the site of the optical measuring axis is known, the site of the resistance measurement is also known, and conversely.

FIG. 5 shows once again the principle of the four-point measuring process, known per se. A detail of a glass plate 4 with a coating 25 is evident herein. With the aid of the four pins, which are placed onto the coating 25 under spring tension, the resistance of the coating 25 is to be measured. For detail cutouts whose width d is much greater than the distance s between the pins 19 to 22 and whose thickness t is much smaller than the distance s, the surface resistance can be calculated according to the formula $$R=(\pi/\ln(2))(U/I)=4.5324(U/I)$$

A conventional value for s is for example s=1.0 mm. The above equation applies if the conditions d>10 s and 10 t<s are fulfilled, which means the equation can be applied for layer thicknesses of $t \leq 100$ μm. This range of applicability is entirely sufficient for measurements on thin layers in the nanometer range.

The fact that the glass plate 4 can be moved in the X-direction and the measuring instruments 12, 13, 17 in the Y direction, makes it possible to determine the transmission, reflection and the resistance for all points on the coated glass plate 4. The transmission and the reflection are in this case available in the form of measurement curves $T=f(\lambda)$ or $R=f(\lambda)$, which in terms of data can only be processed with difficulties.

However, simple processing becomes possible thereby that to each measurement curve a color location in a chromaticity diagram can be assigned, for example in a standard chromaticity diagram CIE 1931, in which the standard chromaticity coordinates are shown in an orthogonal system of coordinates. The measured reflection and transmission curves subsequently only need to be multiplied by the spectral curves of the light source employed and the luminosity curve of the human eye, the so-called $V_\lambda$ curve. Another option for processing the $T(\lambda)$ and $R(\lambda)$ spectral curves comprises determining the wavelength of local maxima and minima. This wavelength is linked to the layer thickness via the index of refraction of the coating, i.e. a shift of the wavelength of local maxima and minima is proportional to a change of the layer thickness.

Thereby that the optical and electrical measured values can be acquired in a very short time over the entire surface of the glass plate 4, it becomes possible to determine the uniformity of the coating 25. This uniformity can be shown optically, for example by representing color fields in a frame corresponding to the size of glass plate 4.

The coating process itself can be regulated on the basis of the determined uniformity distribution of the coating. If it is determined, that, for example, the coating in the upper right corner of the glass plate is too thin, suitable measures can be taken in a sputtering process, for example the voltage can be increased, in order to coat this corner more strongly during the next pass.

It is claimed:

1. A measuring device for measuring at least one optical property of a coating of a substrate, comprising:
    a device for transporting the substrate in a first direction;
    at least one measuring instrument;
    a device for transporting the at least one measuring instrument in a second direction, said second direction being transverse with respect to said first direction; and
    a stationary support for said substrate having a continuous gap along the second direction;
    wherein
    the substrate is provided with a coating at one side thereof;
    the at least one measuring instrument includes at side of the substrate a light transmitter and at the other side of the substrate a light receiver, so that the light of the light transmitter impinges the light receiver through said gap;
    a resistance measuring instrument having a specific distance from the light transmitter is provided at the side of the substrate where the coating is provided; and wherein
    the device for transporting the measuring instrument synchronously transports said resistance measuring instrument in the second direction.

2. A measuring device as claimed in claim 1, wherein the light transmitter is disposed in front of the substrate and the light receiver behind the substrate.

3. A measuring device as claimed in claim 1, wherein a data store is provided, in which the measured optical values with their associated spatial co-ordinates are stored.

4. A measuring device as claimed in claim 1, wherein the resistance measuring instrument is a four-point resistance measuring instrument.

5. A measuring device as claimed in claim 4, wherein the four-point resistance measuring instrument can be moved.

6. A measuring device as claimed in claim 1, wherein a data store is provided, in which the measured resistance values with their associated spatial co-ordinates are stored.

7. A measuring device as claimed in claim 1, wherein for the transport of the plate-form substrate a transporting device is provided, on which rests a side edge of the substrate.

8. A measuring device as claimed in claim 1, wherein the light transmitter is disposed in a housing, in which is also located a light receiver, such that the reflection of the coating can be measured.

* * * * *